US010080512B2

(12) United States Patent
Pham

(10) Patent No.: US 10,080,512 B2
(45) Date of Patent: Sep. 25, 2018

(54) COMBINED CARBON DIOXIDE LASER LATERAL CANTHOTOMY AND FEMTOSECOND LASER-ASSISTED CATARACT SURGERY

(71) Applicant: Randal Tanh Hoang Pham, San Jose, CA (US)

(72) Inventor: Randal Tanh Hoang Pham, San Jose, CA (US)

( * ) Notice: Subject to any disclaimer, the term of this patent is extended or adjusted under 35 U.S.C. 154(b) by 546 days.

(21) Appl. No.: 14/504,780

(22) Filed: Oct. 2, 2014

(65) Prior Publication Data

US 2015/0094619 A1 Apr. 2, 2015

Related U.S. Application Data

(60) Provisional application No. 61/885,640, filed on Oct. 2, 2013.

(51) Int. Cl.
| A61B 5/107 | (2006.01) |
| A61F 9/008 | (2006.01) |
| A61F 9/009 | (2006.01) |

(52) U.S. Cl.
CPC ........ A61B 5/1072 (2013.01); A61F 9/00825 (2013.01); A61F 9/009 (2013.01); *A61F 2009/00887* (2013.01)

(58) Field of Classification Search
CPC ..................................................... A61F 9/008
See application file for complete search history.

(56) References Cited

PUBLICATIONS

Conrad-Hengerer, et al., "Effects of Femtosecond Laser Fragmentation of the Nucleus with Different Softening Grid Sizes on Effective Phaco Time in Cataract Surgery," Journal of Cataract & Refractive Surgery, vol. 38, No. 110, 2012, pp. 1888-1894. http://dx.doi.org/10.1016/j.jcrs.2012.07.023.*
van den Bosch, Willem A., Ineke Leenders, and Paul Mulder. "Topographic anatomy of the eyelids, and the effects of sex and age." British journal of ophthalmology 83.3 (1999): 347-352.*
Jankovic J. Parkinson's disease: clinical features and diagnosis. Journal of Neurology, Neurosurgery & Psychiatry 2008;79:368-376.*
Mahler, Ori, et al. "Laser in situ keratomileusis in myopic patients with congenital nystagmus." Journal of Cataract & Refractive Surgery 32.3 (2006): 464-467.*
International Search Report and Written Opinion in International Application No. PCT/US2014/058783, dated Jan. 9, 2015, 10 pages.
Baker et al., "Lateral Canthal Tendon Suspension Using the Carbon Dioxide Laser", A Modified Technique, dated Dec. 1995 by Elsevier Science Inc., 3 pages.

(Continued)

*Primary Examiner* — Daniel Cerioni
*Assistant Examiner* — Yasmeen S Warsi
(74) *Attorney, Agent, or Firm* — Fish & Richardson P.C.

(57) ABSTRACT

An example method for preparing a surgical site for a femtosecond laser-assisted cataract surgical procedure includes measuring a lower eyelid length of a patient, and determining whether the patient is associated with one or more exposure resistant factors. The method also includes, upon determining that the measured lower eyelid length does not exceeds a threshold length or determining that the patient is associated with at least one exposure resistant factor, performing a canthotomy procedure on the patient.

15 Claims, 2 Drawing Sheets

(56) References Cited

PUBLICATIONS

Goldbaum et al., "The C02 Laser in Oculoplastic Surgery;" Diagnostic and Surgical Techniques, Survey of Ophthalmology vol. 42, No. 3, Nov.-Dec. 1997, 13 pages.
Bosch et al., "Topographic anatomy of the eyelids, and the effects of sex and age", British Journal of Ophthalmology, Mar. 1999;83:347-352 doi:10. 1136/bjo.83.3.347, 7 pages.
Palanker et al., "Femtosecond laser-assisted cataract surgery with integrated optical coherence tomography," Science Translational Medicine, Published Nov. 2010, vol. 2, No. 58, 58ra85, 10 pages.
Dick et al., "Femtosecond laser-assisted cataract surgery in infants," Journal of Cataract & Refractive Surgery, Feb. 11, 2013 (published date: May 2013). vol. 39. No. 5. pp. 665-668.
O'Keefe et al., "LASIK surgery in children," British Journal of Ophthalmology, Jan. 2004, vol. 88, No. 1, pp. 19-21.
Pham et al., "Combined carbon dioxide laser lateral canthotomy and femtosecond laser-assisted cataract surgery," Modern Plastic Surgery, 2013 (published date: Oct. 13, 2013). vol. 3, pp. 130-133.
Sharma et al., "Step by step LASIK surgery," CRC Press, 2003, 1.SBN 1-84184-469-1, pp. 65-67, 5 pages.
Bali et al., "Early experience with the femtosecond laser for cataract surgery," Ophthalmology, 2012. vol. 119, No. 5, pp. 891-899.

\* cited by examiner

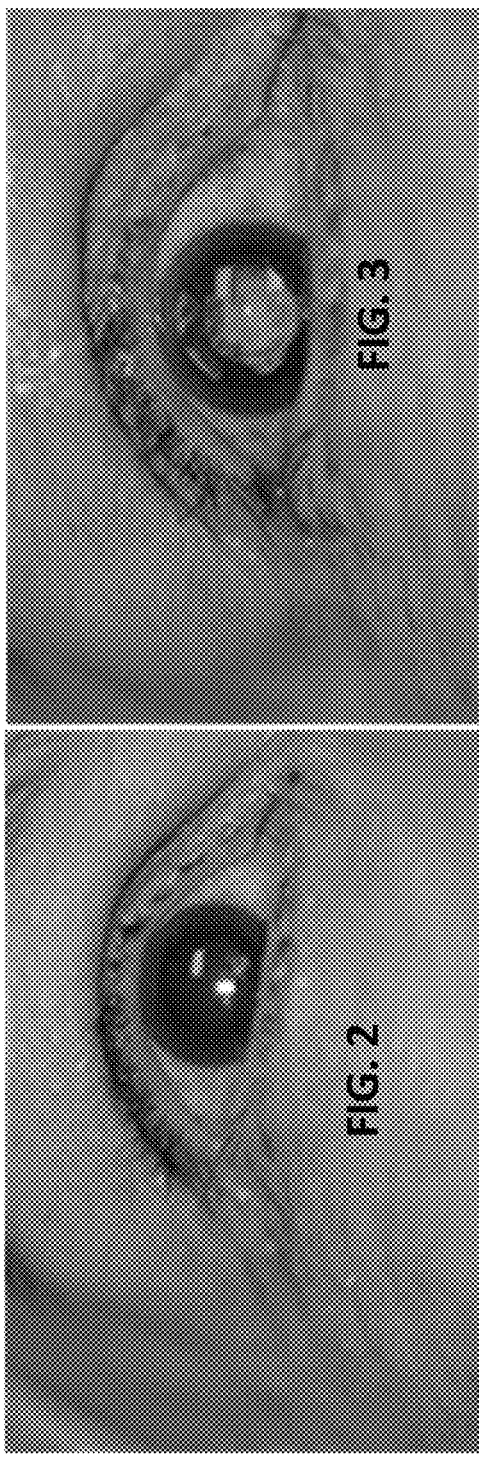
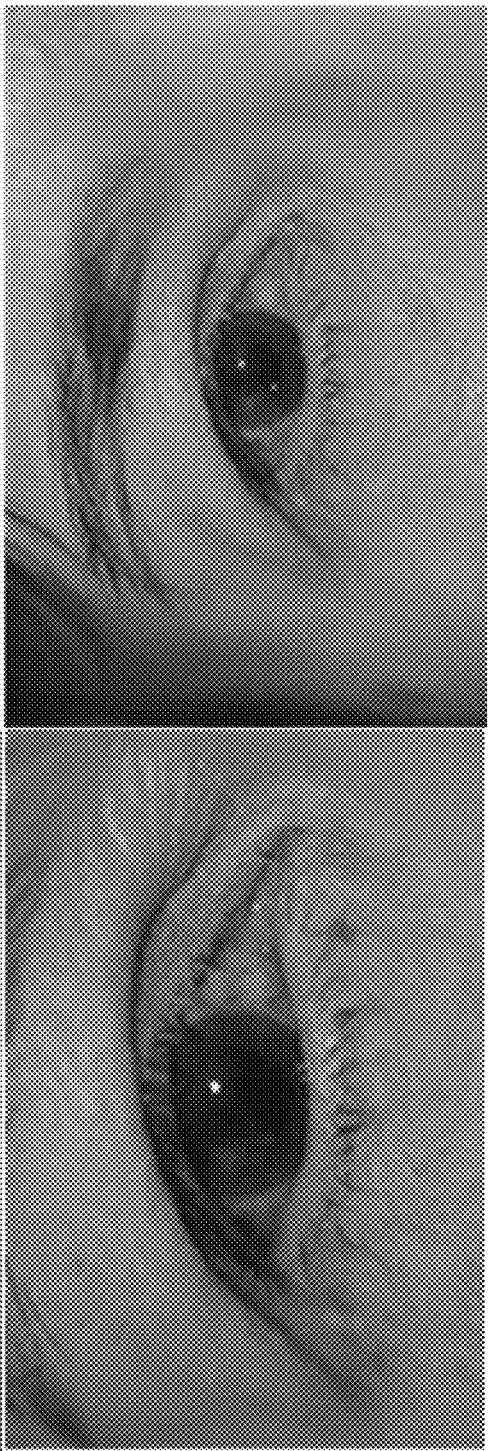

COMBINED CARBON DIOXIDE LASER LATERAL CANTHOTOMY AND FEMTOSECOND LASER-ASSISTED CATARACT SURGERY

TECHNICAL FIELD

This disclosure relates to ophthalmological surgery, and more particularly to preparing surgical sites for laser-assisted cataract surgery.

BACKGROUND

Cataracts is a clouding of the lens inside the eye which leads to a decrease in vision. In many cases, cataracts can be treated surgically. As an example, cataracts can be manually removed (e.g., by a surgeon) by removing the natural lens of the eye that has developed an opacification. Following surgical removal of the natural lens, an artificial intraocular lens implant can be implanted as a replacement.

Femtosecond laser-assisted cataract surgery (FLACS) can be used to assist or replace aspects of manual cataract surgery. The advantages of this technology include, for example, the ability to create a perfectly sized, shaped and centered circular anterior capsular incision, the perfect positioning of the intraocular lens held by a complete edge of the anterior capsule, and the ability to break up the cataract, which in turn reduces phacoemulsification time and energy.

SUMMARY

This disclosure describes implementations of a palpebral fissure-lengthening procedure for preparing a surgical site in connection with an ophthalmological surgical procedure. One or more of the described implementations can be used to improve the overall safety and effectiveness of the surgical procedure. In general, in an aspect, a method for preparing a surgical site for a femtosecond laser-assisted cataract surgical procedure includes measuring a lower eyelid length of a patient, and determining whether the patient is associated with one or more exposure resistant factors. The method also includes, upon determining that the measured lower eyelid length does not exceeds a threshold length or determining that the patient is associated with at least one exposure resistant factor, performing a canthotomy procedure on the patient.

Implementations of these aspect may include or more of the following features.

In some implementations, the canthotomy procedure can be a laser lateral canthotomy procedure.

In some implementations, the exposure resistant factors can include inadequate exposure, irregular conjunctival surface, excessive eye movement, and excessive body movement.

In some implementations, the method can also include fitting a suction ring on the patient's eye after performing the canthotomy procedure.

In some implementations, measuring the lower eyelid length of a patient can include measuring the lower eyelid length of a patient using a measurement device.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 shows a pre-operation photograph of an example patient.

FIGS. 3-5 show post-operation photographs of the example patient shown in FIG. 2.

DETAILED DESCRIPTION

Figure 1:
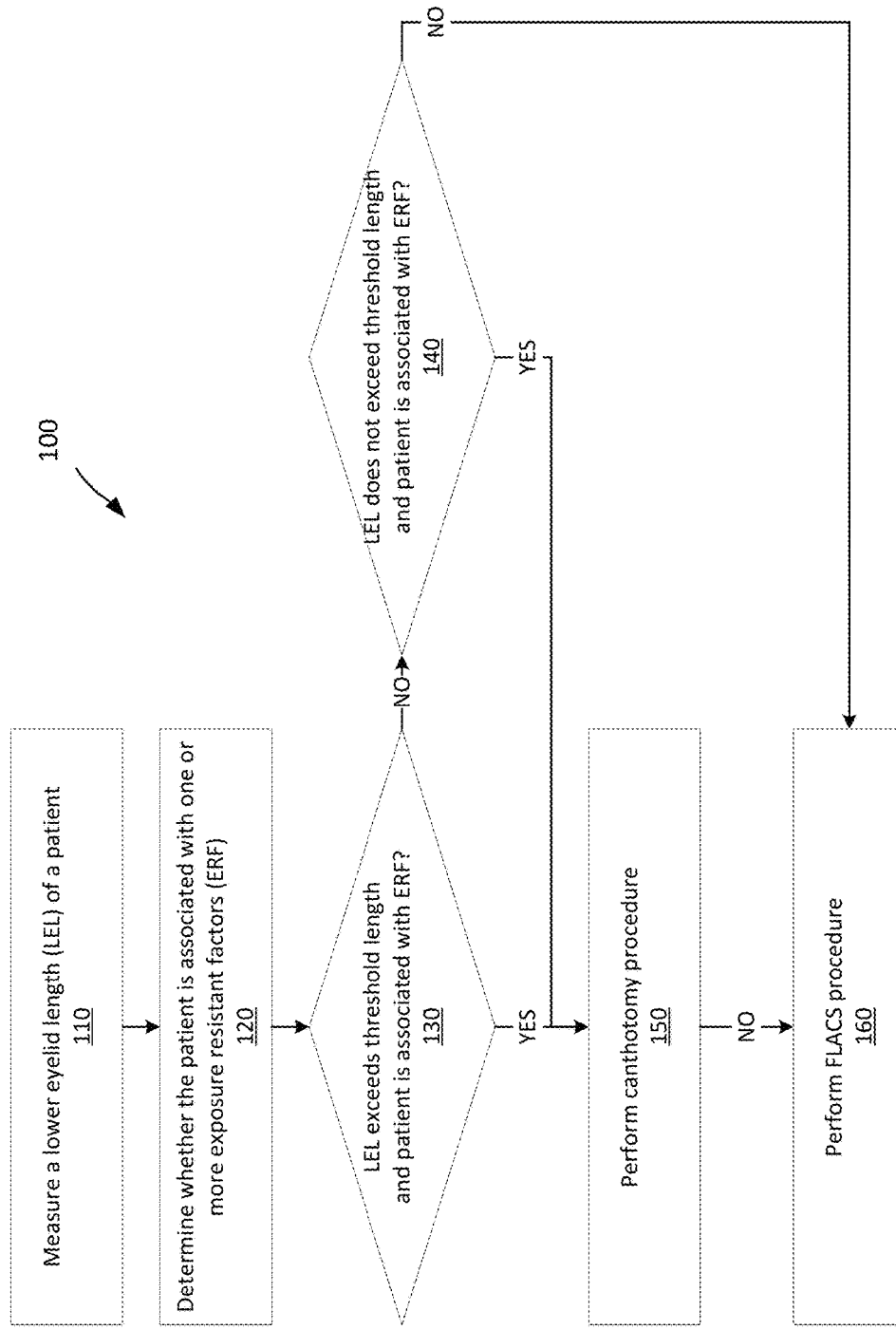
FIG. 1 is a flow chart of an example for preparing a surgical site for a FLACS procedure.

Femtosecond laser-assisted cataract surgery (FLACS) can be used to assist or replace aspects of manual cataract surgery. During an example FLACS procedure, a suction ring is placed directly on the eyeball of a patient, and the laser is attached to the ring using suction. This suction interface stabilizes the eye relative to the laser, such that the laser is secured at a precise location with respect to the eye. Several factors can affect the ability to create a stable laser-eye interface using the suction ring. For example, in cases where the eye has a short palpebral fissure (e.g., short lower eyelid length (LEL)), fitting the suction ring to the eyeball may be difficult (e.g., due to the size of the suction ring). In addition, in some cases, suction can be lost due to various other factors, such as excessive eye, head, and/or body movements.

This disclosure describes implementations of a palpebral fissure-lengthening procedure for preparing a surgical site in order to account for these factors. Implementations of the described procedure can be based on characteristics specific to each patient, such as patient's palpebral fissure dimensions and one or more exposure resistant factors associated with that patient. As an example, for patients with small eyes (e.g., patients having a short palpebral fissure), the patient's palpebral fissure can be lengthened in order to provide a more stable interface between the patient's eye and the laser. Implementations of this procedure can be performed either before an FLACS procedure (e.g., during preparation prior to an FLACS procedure) or during an FLACS procedure (e.g., immediately prior to fitting a suction ring to the eye of a patient). Implementations of this procedure allow docking and completion of a FLACS procedure when it may otherwise be difficult or impossible, and can improve the overall safety and effectiveness of the FLACS procedure.

FIG. 1 shows an example process 100 for preparing a surgical site for a FLACS procedure. The process 100 begins by measuring a lower eyelid length (LEL) of a patient (step 110). As an example, in some implementations, the lower eyelid is measured using a ruler, caliper, or other measuring device. As another example, in some implementations, the patient's eyes are photographed (e.g., using a digital camera), and the patient's LEL is determined based on the photograph (e.g., by estimating dimensions based the camera's optical characteristics, the distance between the camera and the patient's eye, and/or the presence of reference objects in the photograph). As another example, in some implementations, a specialized measurement device (e.g., a measurement device specifically adapted to measure a patient's lower eyelid length) can be used to estimate the lower eyelid length of the patient.

Further, it is also determined whether the patient is associated with one or more exposure resistant factors (ERF) (step 120). ERFs can include one or more factors that may affect stabilization or proper docking of a suction ring to the patient's eye. For example, ERFs can include inadequate exposure. Inadequate exposure can be determined, for example, by determining that when the patient's eye is open and being exposure, an insufficient surface is exposed to allow the suction ring to be placed over the conjunctiva. This can be determined subjectively (e.g., based on a visual estimate), or objectively (e.g., based on a metric that quantifies the exposure of the patient's eye). ERFs can include an irregular conjunctival surface. A patient can be determined to have irregular conjunctival surface, for example, by determining the presence of lesions such as pterygium or pingueculum on the patient's eye. ERFs can also include excessive eye movement. A patient can be determined to have excessive eye movement, for example, by determining that the patient suffers from nystagmus. ERFs can also include excessive body movements. A patient can be determined to have excessive body movement, for example, by determining that the patient suffers from Parkinson's disease. A patient's ERFs can be obtained in a variety of ways. For example, in some implementations, a patient's ERFs can be determined based on previously collected information, for example based on information contained within medical records associated with the patient (e.g., medical records stored on a medical record database). As another example, in some implementations, a patient's ERFs can be determined during the course of the FLACS procedure (e.g., based on a surgeon's observations, measurements, and other tests performed during the FLACS procedure). Although example ERFs and techniques for determining those ERFs are provided above, these are merely illustrative examples. In practice, ERFs can include other factors, either in addition to or instead of those described above. Similarly, other techniques can be used to determine if the presence of ERFs other than those described above.

After the patient's LEL is measured and the patient's ERFs are determined, the patient's LEL is compared against a threshold length. This threshold length corresponds to a minimum length required for an acceptable interface between an eye and the suction ring. This threshold length can depend on the dimensions of the suction ring being used in the FLACS procedure. As an example, in some cases, the threshold length can be equal to approximately one half of the circumference of the suction ring (e.g., within 5%, 10%, 15%, etc. of one half of the circumference of the suction ring). For instance, in some cases, a suction ring is approximately 64 mm (e.g., for the Liquid Optic Interface, Optimedica, Santa Clara, Calif., USA). Accordingly, in some implementations, the threshold length can be approximately 32 mm. Further, as a suction ring can vary in size, depending on the implementation, the threshold length can similarly vary in size to reflect the suction ring's dimensions. Further, although an example relationship is described between a suction ring and the threshold value, in practice, other relationships can also be used, depending on the implementation.

Upon determining that the measured lower eyelid length exceeds a threshold length and determining that the patient is associated with at least one exposure resistant factor (step 130), or upon determining that the measured lower eyelid length does not exceed a threshold length and determining that the patient is associated with at least one exposure resistant factor (step 140), a canthotomy procedure is performed on the patient (step 150). The canthotomy procedure can be a "cold-steel" procedure (e.g., a surgical procedure manually performed by a surgeon using a cutting implement, such as a scalpel or scissor) or a laser procedure (e.g., a laser lateral canthotomy). As an example, an optical anesthetic can be applied to the lateral canthus of the operative eye (e.g., EMLA cream, APP, Lake Zurich, Ill., USA), followed by injection of 0.5 cc of 2% Lidocaine with 1:100,000 epinephrine local anesthetic solution (e.g., Hospira, Lake Forest, Ill., USA) into the lateral canthus of the operative eye. The patient's lateral canthus of the operative eye can be prepped with 5% Betadine solution. For non-laser lateral canthotomy, a hemostat can be placed over the lateral canthus (e.g., for about 5 minutes) to control hemostasis. Tenotomy scissors can be used to make an incision into the lateral canthal commissure to achieve the minimum lower eyelid length required for femtosecond laser docking of the interface eyepiece. Pressure can be applied to the lateral canthus to control hemostasis. For laser lateral canthotomy, a non-reflective metal forceps (e.g., Oculoplastik, Montreal, Quebec, Canada) can be used to protect the eye during laser lateral canthotomy. The lateral canthal commissure can be incised with a laser (e.g., a Nidek Unipulse $CO_2$ laser) set at an appropriate power (e.g., 5 watts in Unipulse mode level III, mid-level between coagulation and cutting modes) to achieve the minimum lower eyelid length required for femtosecond laser docking For laser lateral canthotomy, pressure to the lateral canthus need not be performed. For both cold-steel and laser lateral canthotomies, no wound closure need be performed. In some cases, laser lateral canthotomy provide superior hemostasis when compared to cold-steel procedures. However, in practice, either procedure can be used, depending on the specific implementation.

If it is determined that the measured lower eyelid length does not exceed the threshold length and it is determined that the patient is not associated with at least one exposure resistant factor, the canthotomy procedure is not performed.

After the performing the canthotomy procedure (if necessary), or determining that a canthotomy procedure is not necessary, the FLACS procedure is then performed on the patient (step 160). As an example, a FLACS procedure can be performed using the Catalys Precision Laser System (Optimedica, Santa Clara, Calif., USA) in accordance with accepted operating procedure.

Although example criteria for determining whether to perform a canthotomy are described above (e.g., with respect to steps 130 and 140), this is merely an example. In practice, other criteria can also be used, either in addition to or instead of the criteria described above. For example, in some implementations, a canthotomy can be performed if either the patient's LEL does not exceed the threshold length, or the patient is associated with an ERF. Thus, a canthotomy can be performed if the patient's eye is determined to be too small, if the patient is associated with one or more ERFs that would affect proper interface between the suction ring and the patient's eye, or both. Other criteria and combinations of criteria are also possible, depending on the implementation.

In some implementations, a patient's informed consent is requested prior to performing all or part of the process 100 described above. For example, in some cases, a patient's informed consent can be requested prior to performance of a canthotomy.

Implementations of process 100 can provide various benefits. For example, when faced with a patient having relatively small eyes, a surgeon may have a difficult or impossible time fitting a suction ring onto a patient's eye. By performing the process 100, the surgeon can increase the length of the patient's palpebral fissure in order to provide an acceptable interface between the suction ring and the patient's eye. Thus, implementations of this procedure allow docking and completion of a FLACS procedure when it may otherwise be difficult or impossible, and can improve the overall safety and effectiveness of the FLACS procedure.

Example Study

In order to demonstrate the effectiveness of the process 100, a study was conducted on a cohort of 26 patients (19 women and 7 men) with ages ranging from 45 to 93 years, each having a lower eyelids length equal to or shorter than 32 mm. In this study, each patient underwent a canthotomy procedure, as described above, and subsequently underwent an FLACS procedure.

In this study, charts were reviewed for all patients who had undergone femtosecond laser-assisted cataract surgery with the Catalys Precision Laser System (Optimedica, Santa Clara, Calif., USA) combined with either cold-steel or laser lateral canthotomy with the Nidek Unipulse $CO_2$ laser (Nidek, Fremont, Calif., USA). Demographic data (age, sex, race), use of anticoagulants, indications for lateral canthotomy (exposure resistant factors, or ERFs), and occurrence of post-operative complications (infection, bleeding, non-healing and scarring of lateral canthus, lower eyelid ectropion and formation of conjunctival cysts and cataract surgery complications e.g., ruptured anterior or posterior capsules, dropped nucleus intraoperatively or hypotony, shallow/flat anterior chamber, distorted pupil, intraocular lens dislocation, vitreous herniation, loss of nuclear or cortical materials into the vitreous, retinal detachment and endophthalmitis) were noted for each patient. The minimum lower eyelid length required (MR LEL) for femtosecond laser docking with patient interface-Liquid Optic Interface (LOI) (Optimedica, Santa Clara, Calif., USA) was also determined. Cold-steel and laser lateral canthotomies were compared with respect to successful completion of femtosecond laser-assisted cataract surgery. Statistical significance was assessed using the two-tailed Fisher Exact Test.

Surgical Technique in Example Study

The patient was placed on the Catalys Precision Laser System operating table (Optimedica, Santa Clara, Calif., USA). The Liquid Optic Interface (Optimedica, Santa Clara, Calif., USA) was fitted on the eye. If the Liquid Optic Interface could not be fitted or successful docking could not be achieved, then the patient was prepared for lateral canthotomy. Successful docking was defined as achieving a suction level accepted by the Catalys Precision Laser System and maintained throughout the procedure. The lower eyelid length was measured and marked with a fine tip Devon marking pen (Covidien, Mansfield, Mass., USA). A photograph of the lateral canthus of the operative eye was taken using the Nikon 7100D camera (Nikon, Melville, N.Y., USA). Application of the optical anesthetic EMLA cream (APP, Lake Zurich, IL, USA) to the lateral canthus of the operative eye followed by injection of 0.5 cc of 2% Lidocaine with 1:100,000 epinephrine local anesthetic solution (Hospira, Lake Forest, Ill., USA) into the lateral canthus of the operative eye was performed. The patient's lateral canthus of the operative eye was prepped with 5% Betadine solution. For non-laser lateral canthotomy a hemostat was placed over the lateral canthus for 5 minutes to control hemostasis. Tenotomy scissors were used to make an incision into the lateral canthal commissure to achieve the minimum lower eyelid length required for femtosecond laser docking of the interface eyepiece. Pressure was applied to the lateral canthus to control hemostasis. For laser lateral canthotomy, a non-reflective metal forceps (Oculoplastik, Montreal, Quebec, Canada) was used to protect the eye during laser lateral canthotomy. The lateral canthal commissure was incised with the Nidek Unipulse $CO_2$ laser set at 5 watts in Unipulse mode level III (mid-level between coagulation and cutting modes) to achieve the minimum lower eyelid length required for femtosecond laser docking For laser lateral canthotomy pressure to the lateral canthus was not performed. For both cold-steel and laser lateral canthotomies no wound closure was performed. FLACS was then performed on all patients starting with the fitting of the LOI. The details of FLACS technique was previously described.

Results of Example Study

An adequate exposure for fitting and successful femtosecond laser docking with the Liquid Optic Interface required a minimum lower eyelid length of 32 mm. The minimum lower eyelid length can be a different value, as discussed in greater detail below. Thirty-four eyelids (from 26 patients) were identified to receive lateral canthotomy because of fitting failure or loss of suction; eight patients had bilateral combined lateral canthotomy and cataract surgery performed on different days. The patient ages ranged from 45 to 93 years. Nineteen patients were female and seven were male. Twenty-two were Asians and four were Caucasians. Six patients were on anticoagulants (two on warfarin, four on aspirin). Of these six patients, seven eyelids had lateral canthotomy (1 eyelid with cold-steel and 6 with laser). Post-operative follow up for all patients ranged from 3 to 12 months.

The following exposure resistant factors were identified: small palpebral fissure (32 eyelids), excessive squeezing (1 eyelid), excessive eye movements-nystagmus (2 eyes), excessive body movements (1 eye), abnormal eyelid-dermatochalasis (23 eyelids), entropion (1 eyelid), and abnormal conjunctiva-pingueculum (2 eyes). Other exposure resistant factors are possible.

Referring to FIGS. 2-5, no infection, non-healing or scarring of lateral canthal wound, conjunctival cysts, or ectropion was noted in this study. For example, FIG. 2 shows a pre-op photograph of right eye with cataract and intact lateral canthus. FIG. 3 shows an immediate post-op photograph of right eye after combined LLC and FLACS, and shows completes hemostasis of lateral canthus with no suture placed. FIG. 4 shows a day 1 post-op photograph of right eye after combined LLC and FLACS, and shows complete lateral canthal wound apposition. FIG. 5 shows a day 5 post-op photograph of right eye, and shows complete wound healing of lateral canthus.

One case of lateral canthal bleeding occurred after cold-steel lateral canthotomy in a 93 year-old Asian female patient who was taking anticoagulant (warfarin) at the time of surgery. Docking was successful in this patient but femtosecond laser procedure was not completed because of pupillary constriction after several docking attempts. Conventional cataract surgery, however, was performed. When this patient underwent cataract surgery for the second eye laser lateral canthotomy was performed; no canthal bleeding was noted and femtosecond laser-assisted cataract surgery was completed without complication. Comparison of cold-steel versus laser lateral canthotomy showed that all eyes that had laser lateral canthotomy had completion of femtosecond laser procedure. Two-tailed Fisher Exact Test showed a p-value of 0.0294. No complication either from conventional cataract surgery or from FLACS was identified.

Discussion of Example Study

Patients undergoing femtosecond laser-assisted cataract surgery required a minimum lower eyelid length of 32 mm in order to fit the Liquid Optic Interface over the eye-ball, thus ensuring adequate exposure of the eye to the laser beam. It was noted, however, that the circumference of the LOI provided adequate stabilization once the interface was fitted on the patients' eyes. This stabilization could not be achieved with interfaces that had circumferences smaller than 32 mm. Lack of stabilization could cause loss of suction during femtosecond laser procedure. Stabilization was also affected by the ERFs. The ERFs identified in this study fell into three categories: inadequate exposure, irregular conjunctival surface and excessive eye and/or body movements.

All ERF's for each patient should be identified prior to surgery and these findings should be incorporated into the pre-operative plan. ERF's and lateral canthotomy should be discussed with patients pre-operatively and inform consent obtained. This approach will ease the patient's anxiety and provide the surgeon with a well-defined protocol to follow on the day of surgery. Carbon dioxide laser was found to provide superior hemostasis when compared to cold-steel. A previous study also showed that use of the CO2 laser in the lateral canthal area was safe and effective. The only patient in the present study who developed lateral canthal bleeding had cold-steel canthotomy. This patient, who was the author's first patient to receive FLACS, required additional time for pre- and post-canthotomy hemostasis and multiple attempts were needed to achieve adequate suction for placement of the Liquid Optic Interface. Pupillary constriction occurred in this patient and the femtosecond laser-assisted procedure could not be completed. When the same patient underwent cataract surgery for the second eye laser lateral canthotomy was performed and completion of femtosecond laser procedure was achieved. This case illustrates the importance of hemostasis control should lateral canthotomy become indicated for femtosecond laser-assisted cataract surgery. This patient was one of the six patients in the study who received anticoagulants and one of two who was on warfarin. None of the patients undergoing $CO_2$ laser lateral canthotomy developed canthal bleeding. This observation reinforces the finding that $CO_2$ laser lateral canthotomy, in some cases, provides superior hemostasis compared to cold-steel and is therefore can be indicated in patients who receive anticoagulants. Continued use of anticoagulants is currently considered the standard of care for patients undergoing cataract surgery in many communities in North America, Europe, and Japan.

Although an example study is described above, this is intended only to demonstrate the effectiveness of an example implementation of the surgical site preparation technique. In practice, the disclosed surgical site preparation technique is not solely limited to the example implementation described above.

Further, although the surgical site preparation technique is described above in the context of FLACS procedures, this technique is not limited solely to FLACS procedures. For example, canthotomy (e.g., $CO_2$ laser lateral canthotomy) can be used as an adjunct procedure for conventional cataract surgery and other refractive surgeries such as LASIK, LASEK, PRK, ALK, RLE, EpiLASIK, PRELEX, ICR, phakic intraocular lens implant, AK, RK, etc. In addition, in patients with multiple ERFs, $CO_2$ laser lateral canthotomy can be effective in reducing incidences of suction loss during femtosecond laser refractive surgery. This advantage helps achieve successful completion of femtosecond laser-assisted procedures. As such, $CO_2$ laser lateral canthotomy can be a safe and effective adjunct procedure for femtosecond laser-assisted cataract surgery.

A number of implementations have been described. Nevertheless, it will be understood that various modifications may be made without departing from the spirit and scope of the disclosure. Accordingly, other implementations are within the scope of the following claims.

What is claimed is:

1. A method for preparing a surgical site for a femtosecond laser-assisted surgical procedure, the method comprising:
   measuring a lower eyelid length of a patient;
   determining whether the patient is associated with one or more exposure resistant factors;
   determining at least one of:
      the measured lower eyelid length does not exceed a threshold length, or
      the patient is associated with at least one exposure resistant factor, surgically increasing the lower eyelid length of the patient;
   responsive to determining at least one of the measured lower eyelid length does not exceed a threshold length or the patient is associated with at least one exposure resistant factor, surgically increasing the lower eyelid length of the patient; and
   subsequent to surgically increasing the lower eyelid length of the patient, securing a suction ring onto the patient's eye.

2. The method of claim 1, wherein surgically increasing the lower eyelid length of the patient comprises performing a laser lateral canthotomy procedure.

3. The method of claim 1, wherein the exposure resistant factors comprise: inadequate exposure, irregular conjunctival surface, excessive eye movement, and excessive body movement, and
   wherein the lower eyelid length of the patient is surgically increased responsive to determining that the patient is associated with at least one of inadequate exposure, irregular conjunctival surface, excessive eye movement, or excessive body movement.

4. The method of claim 1 wherein measuring the lower eyelid length of the patient comprises measuring the lower eyelid length of the patient using a measurement device.

5. The method of claim 1, wherein surgically increasing the lower eyelid length of the patient comprises incising a lateral canthal commissure of the patient.

6. The method of claim 5, wherein the lateral canthal commissure of the patient is incised with a scalpel or a scissor.

7. The method of claim 5, wherein the lateral canthal commissure of the patient is incised with a laser.

8. The method of claim 1, wherein the threshold length corresponds to a minimum lower eyelid length associated with securing the suction ring on the patient's eye.

9. The method of claim 1, wherein the threshold length is approximately half of a circumference of the suction ring.

10. The method of claim 1, wherein determining that the patient is associated with at least one exposure resistant factor comprises determining that an insufficient surface of the patient's eye is exposed to allow the suction ring to be placed onto a conjunctiva of the patients' eye, and
    wherein the lower eyelid length of the patient is surgically increased responsive to determining that an insufficient surface of the patient's eye is exposed to allow the suction ring to be placed onto a conjunctiva of the patients' eye.

11. The method of claim 1, wherein determining that the patient is associated with at least one exposure resistant factor comprises determining a presence of a lesion on the patient's eye, and
    wherein the lower eyelid length of the patient is surgically increased responsive to determining the presence of a lesion on the patient's eye.

12. The method of claim 1, wherein determining that the patient is associated with at least one exposure resistant factor comprises determining that the patient suffers from nystagmus, and
    wherein the lower eyelid length of the patient is surgically increased responsive to determining that the patient suffers from nystagmus.

13. The method of claim 1, wherein determining that the patient is associated with at least one exposure resistant factor comprises determining that the patient suffers from Parkinson's disease, and wherein the lower eyelid length of the patient is surgically increased responsive to determining that the patient suffers from Parkinson's disease.

14. The method of claim 1, further comprising:

subsequent to securing the suction ring onto the patient's eye, performing the femtosecond laser-assisted surgical procedure.

15. The method of claim 14, wherein the femtosecond laser-assisted surgical procedure is a cataract surgical procedure.

\* \* \* \* \*